US00PP11238P

United States Patent [19]

Pieters

[11] Patent Number: Plant 11,238

[45] Date of Patent: Feb. 22, 2000

[54] CHRYSANTHEMUM PLANT NAMED 'GEDI YP'

[76] Inventor: Dirk Pieters, Schierveldestraat 3A, Oosnieuwkerke, 8840 Staden, Belgium

[21] Appl. No.: 09/126,002

[22] Filed: Jul. 29, 1998

[51] Int. Cl.[7] ..... A01H 5/00

[52] U.S. Cl. ..... Plt./295

[58] Field of Search ..... Plt./295

*Primary Examiner*—Howard J. Locker

*Attorney, Agent, or Firm*—Christie, Parker & Hale, LLP

[57] ABSTRACT

A new variety of Chrysanthemum producing small yellow daisy-type flowers with yellow ray florets.

1 Drawing Sheet

BACKGROUND OF THE INVENTION

The present invention is directed to a new and distinct variety of Chrysanthemum botanically classified as *Dendranthema grandiflora*. The varietal denomination of the new Chrysanthemum is 'GEDI YP'.

The new variety was discovered as a natural branch mutation of the variety 'Pidoul' (U.S. Plant Pat. No. 10,218) in Staden, Belgium. The new variety has been asexually reproduced by vegetative cuttings in Ventura County, Calif. and the distinguishing characteristics are retained through successive generations of asexual reproduction.

SUMMARY OF THE INVENTION

'GEDI YP' is a Chrysanthemum plant variety that produces a large number of small, yellow daisy-type flowers.

COMPARISON WITH PARENT

The new variety differs from its parent in having flowers with yellow ray florets whereas the ray florets of 'Pidoul' are white.

BRIEF DESCRIPTION OF ILLUSTRATION

The accompanying photograph shows a typical speciman of the new variety with colors being as nearly true as possible with illustrations of this type.

DESCRIPTION OF THE PLANT the following description of the new variety is of specimens grown in a greenhouse in Ventura County, Calif. in the month of April. 'GEDI YP' has not been observed under all possible environmental conditions. The phenotype may vary with variations in the environment such as temperature, light intensity, day length and cultural conditions. the color desgnations herein are general terms are used.

To produce a commercial product the plants may be pinched once about ten days after planting, with center bud removed. No growth regulator was used with plants described. Shelf life of 'GEDI YP' is about 21 days with the response time of about 7 weeks. Desirable growing conditions include average night temperatures of about 62°–64° F and day temperatures of about 70°–75° F and about 2,000–5,000 foot-candles of light.

Plant:

*Habit.*—Mounding, herbaceous perennial, freebranching.

*Height.*—28 cm.

*Number of breaks from pinch.*—About 6 to 7.

*Length of lateral branches.*—About 22 cm.

*Stem color.*—Near 137D.

Foliage:

*Leaf arrangement.*—Alternate.

*Number of leaves per lateral branch.*—About 12 fully expanded leaves.

*Leaf size.*—Length: About 5 cm. Width: About 2.1 cm.

*Leaf shape.*—Ovate.

*Attachment.*—Petioled.

*Leaf apex.*—Acute.

*Base.*—Truncate.

*Margin.*—Palmately lobed.

*Aspect.*—Recurved.

*Surface.*—Top: Lightly pubescent. Bottom: Lightly pubescent.

*Venation.*—Mid-veins prominent on underside. Color: Underside: Near 137C. Upperside: Near 146C.

*Petiole.*—Length: About 1.4 cm. Color: Near 146C. Mature leaf: Top: Near 137A. Bottom: Near 138B. Young Leaf: Top: Near 137B. Bottom: Near 138B.

Flower:

*Inflorescence form.*—Cyme.

*Flower form.*—Daisy-type.

*Number of blooms per branch.*—About 18.

*Diameter of fully expanded bloom.*—About 3 cm.

*Depth of fully expanded bloom.*—About 1 cm.

*Diameter of disc.*—About 1.3 cm.

*Sepal number.*—About 25. Color: Near 137C. Length: About 0.7 cm. Width: About 0.4 cm.

*Penduncle.*—Length: Uppermost peduncle: About 4 cm. Lateral peduncle: About 7 cm. Aspect: Weak, slightly undulating. Surface: Pubescent. Color: Near 137D.

*Flower bud* (*when just showing color*).—Color: Near 7B. Diameter: About 0.9 cm. Height: About 0.7 cm. Shape: Flattened sphere.

*Ray florets.*—Number per flower: About 28. Texture: Matte. Shape: Oblanceolate. Apex: About 2 to 3 irregular obtuse lobes. Base: Tapered. Margin: Entire Aspect: Slightly curved. Length: About 1.4 cm. Width: About 0.4 cm.

*Disc florets.*—Number per flowers: About 140. Texture: Shiny. Shape: Cylindrical, fluted apex. Length: About 0.6 cm.

*Fragrance.*—Moderate.

Flower color:

*General flower coloration.*—Yellow daisy-type with a yellow/orange disc.

*Ray florets, top side.*—Immature: Near 9A. Mature: Near 6A. Fading: Near 9C.

*Ray floret, under side.*—Immature: Near 9B. Mature: Near 8A. Fading: Near 8B.

*Disc florets.*—Immature: Near 15B. Mature: Near 15B. Fading: Near 15C.

*Changes as the flower ages.*—Ray florets lighten in color, considerable pollen is released making the disc appear darker orange-yellow.

Reproductive organs:

*Ray florets*—Pistillate. Stigma shape: 2 branched. Stigma color: Near 7A. Style length: About 0.5 cm. Style color: Near 1D.

*Disc florets.*—Stigma shape: 2 branched. Stigma color: Near 12A. Style length: About 0.3 cm. Style color: Near 154C. Stamen number: About 5. Anther length: About 0.2 cm. Pollen color: Near 17B. Pollen quantity: Abundant.

What is claimed is:

1. A new and distinct Chrysanthemum plant of the variety substantially as herein shown and described.

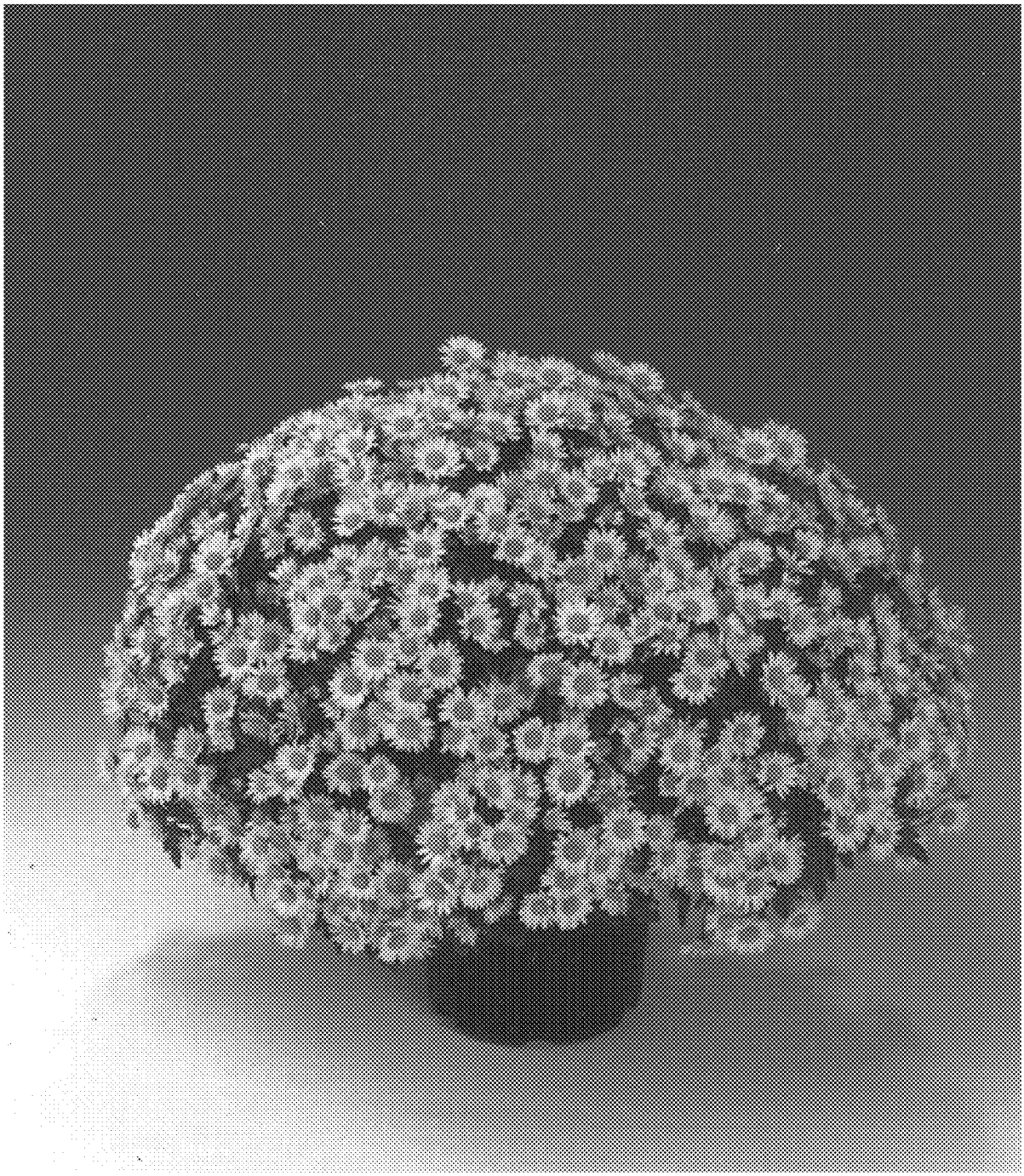

* * * * *